(12) United States Patent
Suwa (10) Patent No.: US 9,104,097 B2
(45) Date of Patent: Aug. 11, 2015

(54) RADIOGRAPHIC APPARATUS

(75) Inventor: Hidetomo Suwa, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 400 days.

(21) Appl. No.: 13/384,651

(22) PCT Filed: Sep. 15, 2010

(86) PCT No.: PCT/JP2010/066466
§ 371 (c)(1),
(2), (4) Date: Jan. 18, 2012

(87) PCT Pub. No.: WO2011/037153
PCT Pub. Date: Mar. 31, 2011

(65) Prior Publication Data
US 2012/0195409 A1     Aug. 2, 2012

(30) Foreign Application Priority Data

Sep. 25, 2009  (JP) .................................. 2009-221441

(51) Int. Cl.
*G03B 42/04* (2006.01)
*G01T 1/16* (2006.01)
(Continued)

(52) U.S. Cl.
CPC .............. *G03B 42/04* (2013.01); *A61B 6/4283* (2013.01); *G01T 1/244* (2013.01)

(58) Field of Classification Search
CPC ....... G03B 42/04; G01T 1/244; A61B 6/4283
USPC .............................. 378/98.8, 189; 250/370.09
See application file for complete search history.

(56) References Cited

U.S. PATENT DOCUMENTS

| | | | | |
|---|---|---|---|---|
| 4,403,150 | A | * | 9/1983 | Kurihara et al. .......... 250/370.07 |
| 5,804,832 | A | | 9/1998 | Crowell et al. ............... 250/580 |
| 6,825,472 | B2 | * | 11/2004 | Endo ........................ 250/370.09 |
| 2002/0014594 | A1 | | 2/2002 | Endo ........................ 250/370.09 |

(Continued)

FOREIGN PATENT DOCUMENTS

| | | |
|---|---|---|
| CN | 1234528 | 11/1999 |
| CN | 1540442 | 10/2004 |

(Continued)

OTHER PUBLICATIONS

Office Action issued Jan. 20, 2014 in counterpart Japanese patent application 2009-221441, with translation.

(Continued)

*Primary Examiner* — Glen Kao
(74) *Attorney, Agent, or Firm* — Fitzpatrick, Cella, Harper & Scinto (57) ABSTRACT

A radiographic apparatus including an X-ray generating means which irradiates an object with X-rays, the apparatus comprises a first housing which includes an X-ray reception unit formed by a member having a higher X-ray transmittance than a frame member, a buffer material which is placed on the first housing and reduces a load on the X-ray generating means, an X-ray detection sensor which is placed on the buffer material and detects X-rays transmitted through the object, a support member whose support surface to support the X-ray detection sensor is placed on the X-ray detection sensor, and a second housing which includes a concave portion engaging with the convex portion formed on the support member and constrains movement of the support member.

11 Claims, 8 Drawing Sheets (51) Int. Cl.
   *A61B 6/00* (2006.01)
   *G01T 1/24* (2006.01)

(56) References Cited

U.S. PATENT DOCUMENTS

| | | | |
|---|---|---|---|
| 2004/0149930 A1 | 8/2004 | Ando | 250/484.4 |
| 2004/0211909 A1 | 10/2004 | Watanabe | 250/370.11 |
| 2009/0065703 A1 | 3/2009 | Jadrich et al. | 250/370.11 |
| 2011/0163240 A1 | 7/2011 | Suwa et al. | 250/370.09 |
| 2012/0039441 A1 | 2/2012 | Suwa et al. | 378/62 |

FOREIGN PATENT DOCUMENTS

| | | |
|---|---|---|
| JP | S60-196495 | 10/1985 |
| JP | 2006-311575 | 11/2006 |
| JP | 3848288 | 11/2006 |

OTHER PUBLICATIONS

Office Action issued Mar. 27, 2014 in counterpart Chinese patent application 201080041713.2, with translation.

* cited by examiner

RADIOGRAPHIC APPARATUS

TECHNICAL FIELD

The present invention relates to a radiographic apparatus.

BACKGROUND ART

Conventionally, apparatuses which obtain radiographic images of objects by irradiating the objects with X-rays and detecting the intensity distributions of X-rays transmitted through the objects have been widely and generally used in the fields of industrial non-destructive testing and medical diagnosis. As a general method for such imaging, a film/screen method using X-rays is available. This method images an object by using a combination of a photosensitive film and a phosphor having sensitivity to X-rays. Rare-earth phosphor sheets which emit light upon application of X-rays are held in tight contact with the two surfaces of a photosensitive film. The phosphor converts X-rays transmitted through an object into visible light. The photosensitive film then captures the light. The method then develops, by chemical process, the latent image formed on the film, thereby visualizing the image.

The recent advances in digital technology have popularized the scheme of obtaining high-quality radiographic images by converting the intensity distribution of X-rays transmitted through an object into an electrical signal, detecting it, processing it, and then reproducing the resultant information as a visible image on a monitor or the like. As such a method of converting a radiographic image into an electrical signal, there has been a proposed radiographic image recording/reproduction system which temporarily stores X-rays transmitted through an object as a latent image in a phosphor, photoelectrically reads out the latent image by irradiating the phosphor with excitation light such as a laser beam, and then outputs the readout image as a visible image.

In addition, with the recent advances in semiconductor process technology, there has been developed an apparatus for capturing a radiographic image in the same manner as described above by using a semiconductor sensor. These systems have very wide dynamic ranges as compared with conventional radiographic systems using photosensitive films, and can obtain radiographic images which are robust against the influences of variations in the X-ray dose upon exposure. At the same times, unlike the conventional photosensitive film scheme, this method need not to perform any chemical process and can instantly obtain an output image.

Recently, a portable radiographic apparatus has also been developed, which is used when it is necessary to perform imaging in an arbitrary imaging posture. This portable radiographic apparatus may directly receive the load of an object as a static load or may possibly receive a shock load when the apparatus is dropped during transportation. As described above, the portable radiographic apparatus is required to have certain strength, enough to stand the load acting on the apparatus while protecting the internal X-ray detection unit of the apparatus.

Recently, a portable imaging apparatus like that disclosed in Japanese Patent No. 3848288 has been proposed. The X-ray detection sensor is supported on a base having high levels of strength. This base is fixed to an exterior on the lower side. The lower surface of the base has a plurality of concave portions, to which a plate member made of a carbon material is bonded to secure the strength of the sensor.

In addition, Japanese Patent Laid-Open No. 2006-311575 has proposed an apparatus which has a gas-filled vessel placed between the X-ray detection sensor and the housing to protect the sensor.

In general, improving the strength of an apparatus itself while protecting the interior of the apparatus will increase the weight and size of the apparatus itself. A portable radiographic apparatus is sometimes inserted between an operating table or the like and an object to image it on a table in an X-ray room, on a bed in a hospital ward, or on an operating table in an operating room. For this reason, the radiographic apparatus is required to be as thinner as possible to reduce the discomfort experienced by patients. When inserting the radiographic apparatus between the operating table or the like and the object at the time of imaging, an X-ray technician who operates the radiographic apparatus needs to hold the apparatus with one hand. When using a radiographic apparatus on a nursing cart on a side of a bed in a hospital ward, in particular, the technician needs to set the radiographic apparatus while holding the posture of a patient by himself/herself. The apparatus is therefore required to be smaller and lighter for a reduction in load on the technician as well.

As described above, in the case of the conventional radiographic apparatus, to improve the strength of the apparatus itself in consideration of the protection of the apparatus, it is necessary to increase the weight and size of the apparatus itself. On the other hand, in consideration of reduction in the discomfort experienced by a patient, it is required to reduce the thickness of the apparatus, whereas in consideration of reduction in the load on an operator, it is required to reduce the weight of the apparatus. That is, the conventional radiographic apparatus has such contradictory challenges.

In the apparatus disclosed in Japanese Patent No. 3848288, the support structure of the X-ray detection sensor is fastened to the exterior housing with screws to restrict the movement of the X-ray detection sensor inside the apparatus. Consider this apparatus in the thickness direction. In this case, in consideration of the head of each screw, the thickness of the housing, and a sufficient engaging amount of each screw, the apparatus needs to have a certain thickness on the rear side of the X-ray detection sensor, leading to a limitation in reduction in thickness.

The apparatus disclosed in Japanese Patent Laid-Open No. 2006-311575 is characterized in that even when the housing deforms upon application of an external shock or the like, the X-ray detection sensor inside is protected, and the housing has stability. In order to protect the X-ray detection sensor in the housing while permitting the deformation of the housing, a sufficient space must be secured between the housing and the X-ray detection sensor. This leads to a limitation in terms of reduction in the thickness.

SUMMARY OF INVENTION

The present invention provides a radiographic apparatus which achieves reductions in the thickness and weight of the apparatus and provides excellent convenience while securing a strength necessary to protect the X-ray detection sensor placed inside the apparatus.

According to one aspect of the present invention, there is provided a radiographic apparatus including an X-ray generating means which irradiates an object with X-rays, the apparatus comprising:

a first housing which includes an X-ray reception unit formed by a member having a higher X-ray transmittance than a frame member;

a buffer material which is placed on the first housing without any gap and reduces a load on the X-ray generating means in an X-ray irradiation direction;

an X-ray detection sensor which is placed on the buffer material without any gap and detects, via the X-ray reception unit, X-rays transmitted through the object;

a support member whose support surface to support the X-ray detection sensor is placed on the X-ray detection sensor without any gap, with at least one convex portion being formed on a surface on an opposite side to the support surface; and a second housing which includes a concave portion engaging with the convex portion formed on the support member and constrains movement of the support member in a direction perpendicular to the X-ray irradiation direction as the convex portion engages with the concave portion.

The present invention can provide a radiographic apparatus which achieves reductions in the thickness and weight of the apparatus and provides excellent convenience while securing a strength necessary to protect the X-ray detection sensor placed inside the apparatus.

Further features of the present invention will become apparent from the following description of exemplary embodiments (with reference to the attached drawings).

DESCRIPTION OF EMBODIMENTS

The embodiments of the present invention will be described in detail below with reference to the accompanying drawings.

(First Embodiment)

Figure 1A:
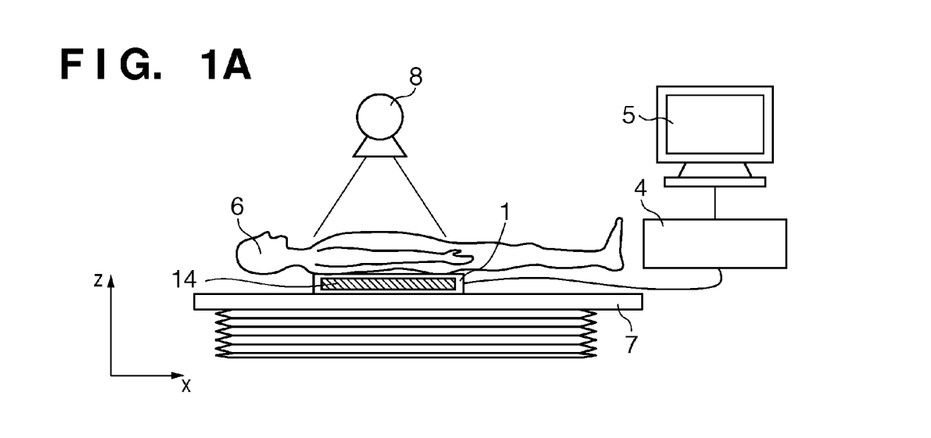
FIG. 1A is a view for explaining an outline of a radiographic system.

An outline of a radiographic system using a radiographic apparatus will be described with reference to FIG. 1A. A radiographic apparatus 1 incorporates an X-ray detection sensor 14. An X-ray generator 8 is provided above radiographic apparatus 1. The X-ray generator 8 irradiates an object 6 with X-rays. The X-rays transmitted through the object 6 are converted into visible light through a phosphor. Photoelectric conversion elements arrayed in a two-dimensional matrix pattern detect the visible light as electrical signals. The radiographic apparatus 1 includes a control unit which controls the overall apparatus. This control unit controls the operation of, for example, reading out the electrical signals detected by the photoelectric conversion elements, processing the readout data, and transferring the images based on the electrical signals. An image processing unit 4 digitally processes the images transferred from the control unit of the radiographic apparatus 1. A monitor 5 then displays a radiographic image of the object 6. Unlike the radiographic image recording/playback system which reads out images after processing, this system has a merit that it can instantly displays an image on a monitor. The radiographic apparatus 1 can be formed as a portable radiographic apparatus, which is suitable for imaging of the object 6 in an arbitrary imaging posture.

A sectional structure of the radiographic apparatus 1 according to the first embodiment will be described with reference to FIGS. 1B and 1C. A first housing 11 is a housing on the X-ray incident side, and is made of a high-rigidity material (frame member 19) such as an aluminum alloy or a magnesium alloy which is light weighted and strong. In order to acquire a high-quality image with a high S/N ratio, it is necessary to cause the X-rays emitted from the X-ray tube of the X-ray generator 8 and transmitted through the object 6 to losslessly reach the X-ray detection sensor. For this reason, the X-ray reception unit of the first housing 11, which is placed above the X-ray incident side projection surface of the X-ray detection sensor 14 (to be described later) and receives the X-rays emitted from the X-ray generator 8, is required to have an X-ray transmittance higher than that of the frame member 19. The first embodiment uses, for the X-ray reception unit of the first housing 11, CFRP 12 which is a carbon fiber reinforced plastic having a higher X-ray transmittance than the frame member 19. The CFRP 12 is bonded to the frame member 19 of the first housing 11 with an adhesive.

For the purpose of increasing the X-ray transmittance and reducing the weight, the CFRP 12 used is as thin as about 1 mm. For this reason, the CFRP 12 cannot alone bear the load of the object at the time of imaging, and hence bends. Consequently, the load acting on the CFRP 12 will directly act on the X-ray detection sensor 14 located below the CFRP 12. To prevent loads including shocks from directly acting, as local loads, on the X-ray detection sensor 14, a buffer material 13 made of a foaming agent such as a silicon- or urethane-based material is placed between the CFRP 12 and the X-ray detection sensor 14 so as to reduce loads.

The X-ray detection sensor 14 includes an aluminum sheet to protect a phosphor from the X-ray incident side and the phosphor to convert radiation into visible light. The X-ray detection sensor 14 also includes photoelectric conversion elements arrayed in a matrix pattern to convert visible light into an electrical signal and a substrate on which the photoelectric conversion elements are formed. The X-ray detection sensor 14 includes an aluminum sheet, phosphor, photoelectric conversion elements, and substrate which are stacked on each other.

The electrical signals converted by the photoelectric conversion elements are connected to a signal processing circuit board 17 via a flexible circuit board 18 placed on a side surface of the X-ray detection sensor 14.

A support member 15 is a member to support the X-ray detection sensor 14. For this member, it is possible to use a material having high rigidity such as an aluminum alloy, magnesium alloy, or CFRP, which are lightweight and strong. The support member 15 is joined to the X-ray detection sensor 14 with an adhesive member such as a double-faced tape. Since the support member 15 is a thin plate member, when a load externally acts on the first housing 11, e.g., when an object is placed on the first housing 11, the support member 15 does not have a strength function good enough to protect the X-ray detection sensor 14 from damage. For this reason, an external load is directly transferred to a second housing 16 located on the rear when viewed from the X-ray incident side of the support member 15. In this manner, a thin material is used for the support member 15 to achieve reductions in the thickness and weight of the apparatus.

Figure 1B:
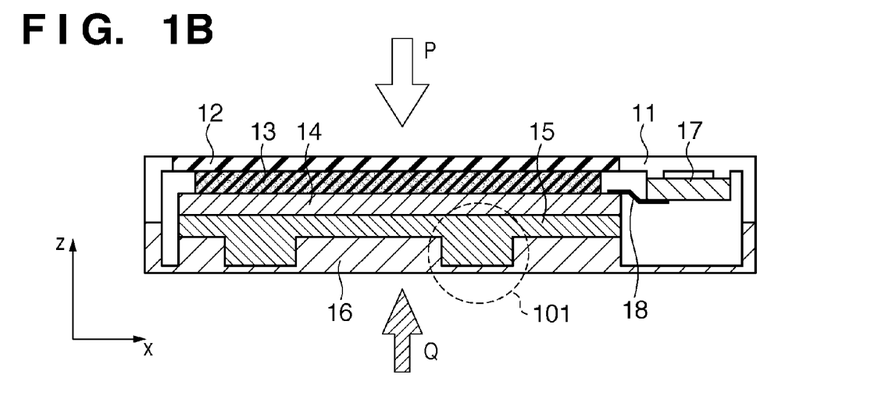
FIG. 1B is a sectional view showing the arrangement of a radiographic apparatus according to the first embodiment.
Figure 2A:
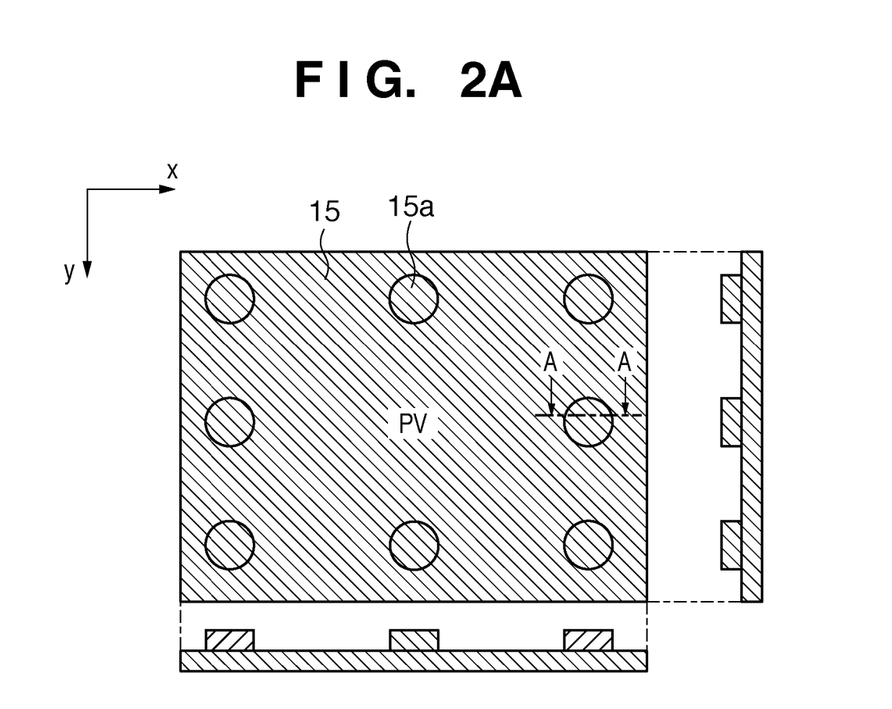
FIG. 2A is a view showing an example of a support member used in the radiographic apparatus according to the first embodiment.
Figure 2B:
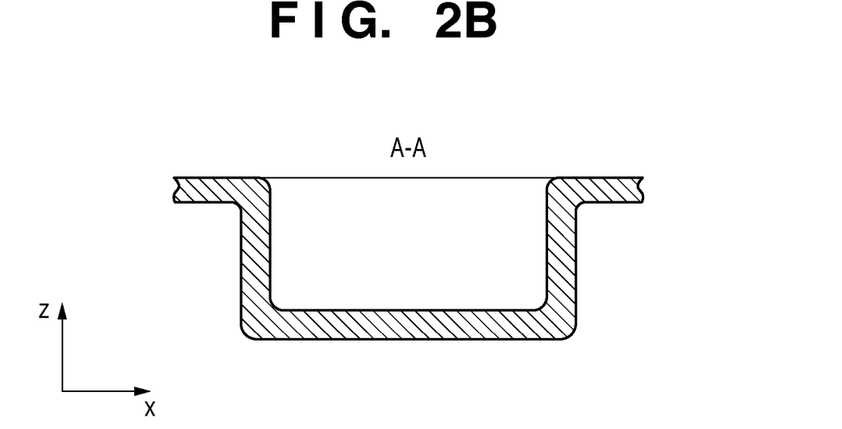
FIG. 2B is a partial sectional view of the support member shown in FIG. 2A.

As shown in FIGS. 2A and 2B, the support member 15 has several convex portions 15a protruding toward the second housing 16. FIG. 2A shows an example in which eight convex portions are formed. A front view PV of FIG. 2A is a view taken when the support member 15 is seen from the direction of an arrow Q in FIG. 1B. In this example, when seen from the direction of the arrow Q, each convex portion has a columnar shape. FIG. 2B is a sectional view taken along a line A-A of each convex portion in FIG. 2A. Each convex portion is formed by deforming part of the support member 15 into a convex shape by drawing or the like. However, it is possible to form convex shapes as discrete parts and fix them on the support member 15 having a flat plate shape. The positions and number of convex portions are determined in consideration of the magnitude and direction of a shock load acting on the apparatus.

The second housing 16 is located on the opposite side (the rear surface side) to the X-ray detection sensor 14 when viewed from the X-ray incident side, and is made of a material having high rigidity such as an aluminum alloy or magnesium alloy which is light weighted and strong like the first housing 11. Concave portions are formed on the support member 15 side of the second housing 16 to engage with the convex portions provided on the support member 15. Bringing the second housing 16 into contact with the support member 15 will support a load in the vertical direction (z-axis direction). The external load applied when an object is placed on the first housing 11 is entirely received by the second housing 16 through the buffer material 13, the X-ray detection sensor 14, and the support member 15. The second housing 16 has a bending rigidity higher than an allowable stress value which is the limit value of the bending stress of the X-ray detection sensor 14.

The engaging structure in which the concave portions formed in the second housing 16 engage with the convex portions formed on the support member 15 restricts the movement of the X-ray detection sensor 14 in a plane direction (x-y plane), with the X-ray incident direction being a normal, inside the apparatus. The position and posture of the X-ray detection sensor 14 are maintained in the plane direction inside the radiographic apparatus. In addition, the CFRP 12, the buffer material 13, the X-ray detection sensor 14, the support member 15, and the second housing 16 which are jointed to the frame member 19 of the first housing 11 are stacked on each other without any gap when viewed from the X-ray incident direction (z direction). Stacking them without any gap will restrict the movement of the X-ray detection sensor 14 in the X-ray incident direction (z direction) and can maintain its position and posture.

In practice, since it is difficult to stack rigid bodies without any gap, a pressure is kept applied to the buffer material 13, which is made of a foaming agent such as a silicon- or urethane-based material, so as to compress it in the X-ray incident direction. The resultant repulsive force is used to press the X-ray detection sensor 14, the support member 15, and the like in the X-ray incident direction (z direction) so as to eliminate gaps.

Figure 3A:
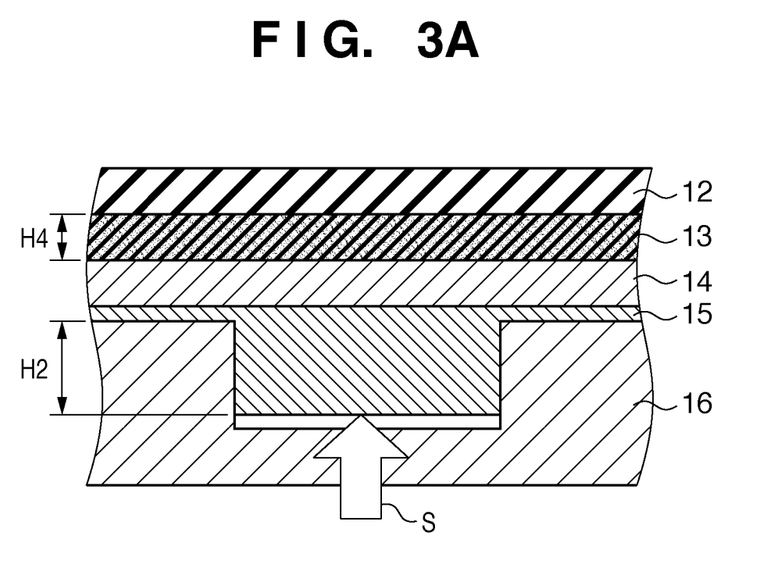
FIG. 3A is a partial enlarged view of FIG. 1A.

The buffer material 13 is made of a foaming agent such as a silicon- or urethane-based material, and hence deforms upon receiving a load. FIG. 3A is an enlarged view of a portion 101 in FIG. 1B. Referring to FIG. 3A, when the second housing 16 is dropped, the support member 15 receives a shock load S.

Figure 3B:
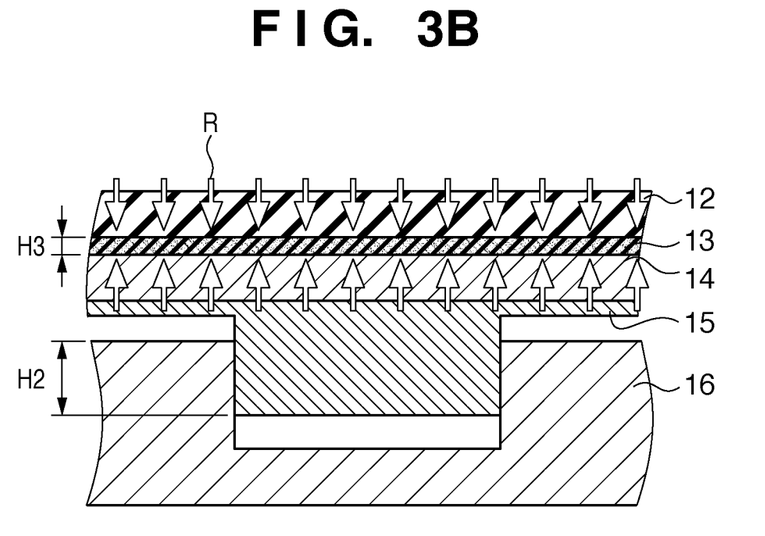
FIG. 3B is a view for explaining the deformation of a buffer material.

The buffer material 13 is placed while receiving a first compression force (load R) from the contact surface with the first housing 11 in the X-ray irradiation direction and a second compression force from the contact surface with the X-ray detection sensor 14 in a direction opposite to that of the first compression force. The height by which each convex portion engages with a corresponding concave portion is larger than the amount of deformation caused in the buffer material 13 by the first and second compression forces. Upon receiving the load R, the buffer material 13 is compressed from a thickness H4 in the initial state to H3, as shown in FIG. 3B. Letting H1 (=H4−H3) be the maximum compression amount and H2 be the length (engaging amount) of each convex portion formed on the support member 15 which engages with a corresponding concave portion formed in the second housing 16, it is necessary to satisfy the relation of H1<H2. When the maximum compression amount H1 of the buffer material 13 becomes larger than the engaging amount H2, the concave portion of the second housing 16 disengages from the convex portion of the support member 15. Disengaging these portions will produce a degree of freedom of movement of the X-ray detection sensor 14 in the plane direction (perpendicular to the X-ray irradiation direction) with the X-ray irradiation direction being a normal. This makes it impossible to hold the X-ray detection sensor 14 in the plane direction.

When disengagement occurs upon reception of a shock such as a drop shock, the X-ray detection sensor 14 moves inside the radiographic apparatus and may collide with the inner wall of the first housing 11 or second housing 16. As a result, the X-ray detection sensor 14 may be damaged. If, however, H1<H2 is satisfied, the X-ray detection sensor 14 does not move in the plane direction with the X-ray incident direction being a normal.

The above structure can maintain the position and posture of the X-ray detection sensor 14 without fixing it to the housing, and can reliably protect the X-ray detection sensor 14 even upon receiving an external load or shock. It is also possible to reduce the size of the radiographic apparatus in the thickness direction by reducing the thickness of the buffer material 13 and reducing the engaging amount between each convex portion of the support member 15 and the corresponding concave portion of the second housing 16 while satisfying the relation of H1<H2. This can implement a thinner radiographic apparatus.

Figure 1C:
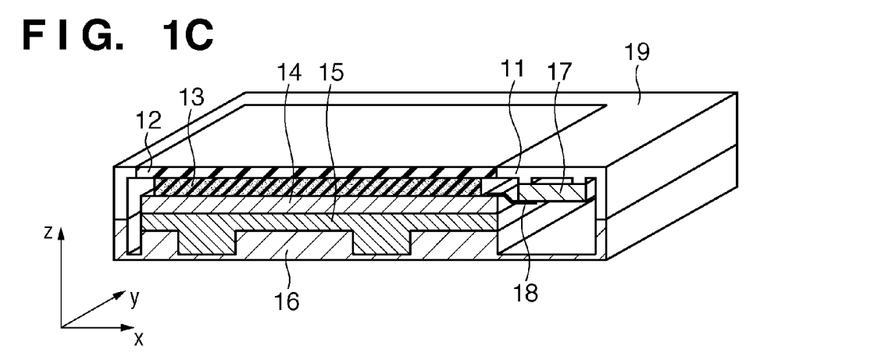
FIG. 1C is a sectional perspective view of the radiographic apparatus.
Figure 6A:
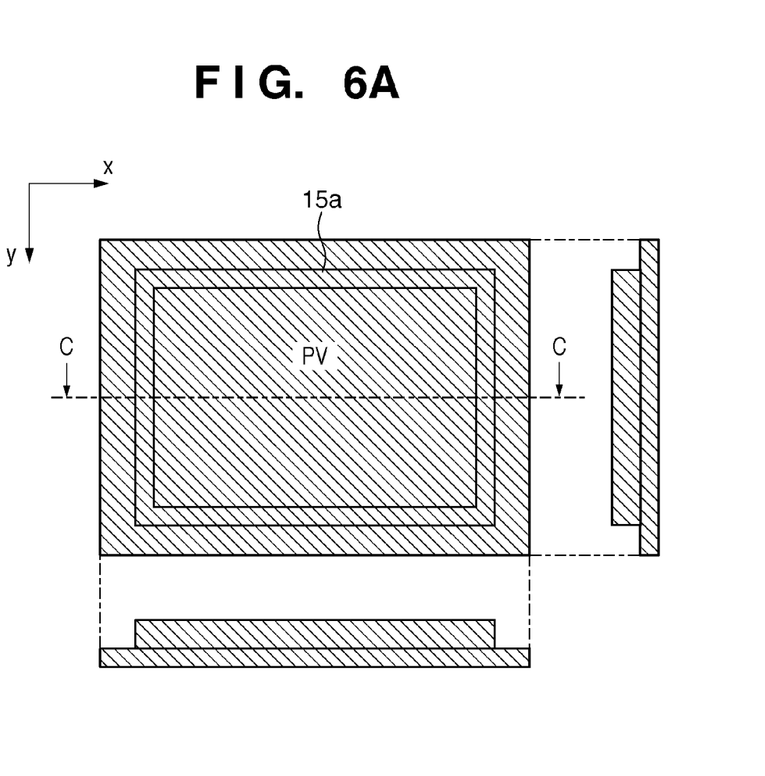
FIGS. 6A and 6B are views showing an example of the shape of the convex portion of the support member used in the radiographic apparatus according to the first embodiment.
Figure 6B:
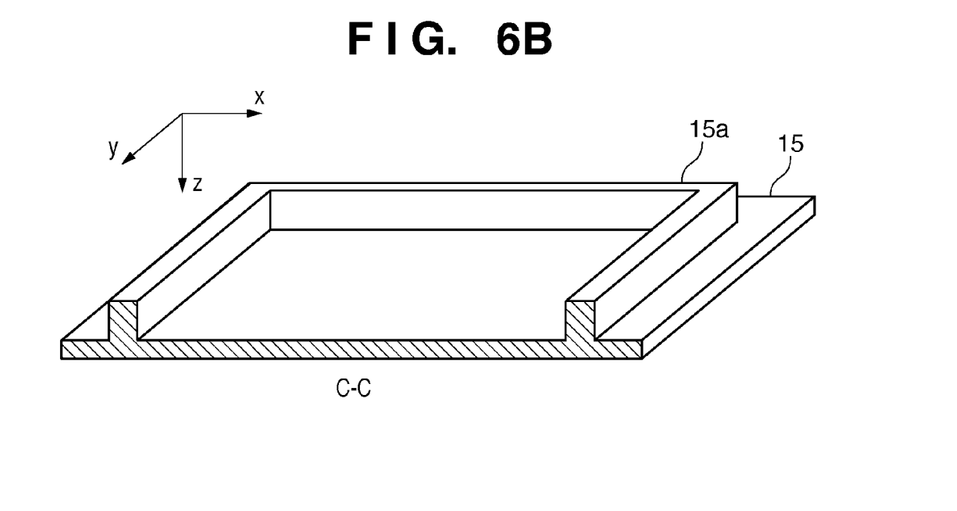

In the first embodiment, a projection view of each convex portion of the support member 15 shows a circular shape when viewed from the arrow Q direction in FIG. 1B. However, the gist of the present invention is not limited to this shape. For example, each convex portion may have another shape such as a cruciform shape or a rectangular shape like that shown in FIGS. 6A and 6B as long as it has the same function as that described in the first embodiment. Using such a structure can provide a radiographic apparatus which achieves reductions in the thickness and weight of the apparatus, and provides excellent convenience while securing strength necessary to protect the X-ray detection sensor placed inside the apparatus.

(Second Embodiment)

Figure 4A:
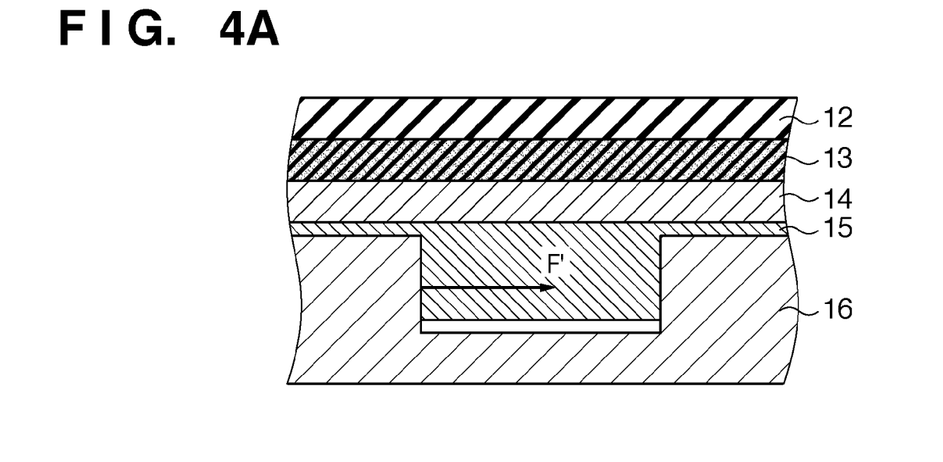
FIGS. 4A to 4C are views exemplarily showing the forces acting on a support member used in a radiographic apparatus according to the second embodiment.
Figure 4B:
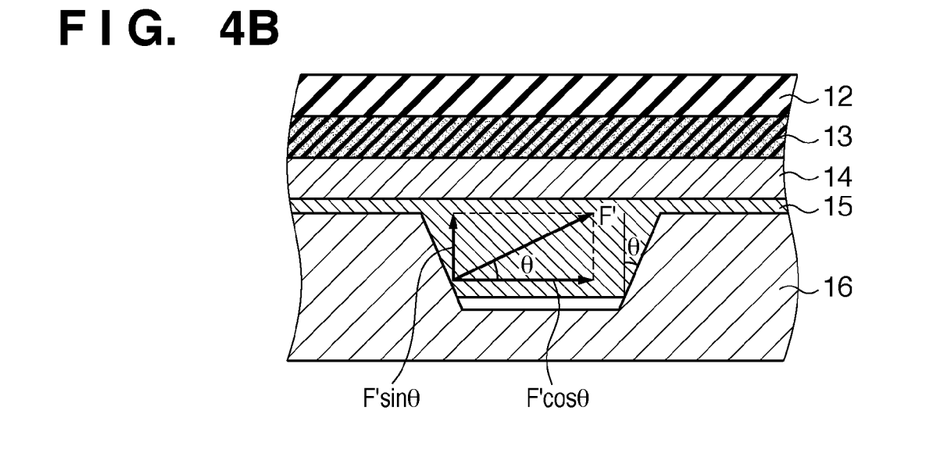
Figure 4C:
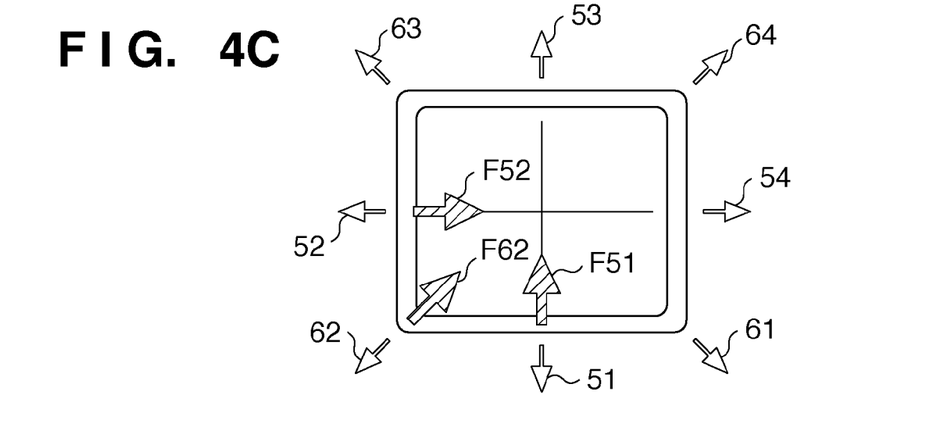

Forces acting on a support member used in a radiographic apparatus according to the second embodiment will be exemplarily described with reference to FIGS. 4A to 4C. FIG. 4B shows an example of a sectional shape of a convex portion formed on a support member 15 used in the radiographic apparatus according to the second embodiment. The convex portion does not have a columnar shape but has a circular truncated conical shape which is tapered such that the diameter of the distal end portion of the convex portion is smaller than that of proximal end portion. The side surfaces of each concave portion formed in a second housing 16 have slopes engaging with the tapered portions. FIG. 4C shows a state viewed from the direction of an arrow P in FIG. 1B. Consider a case in which the radiographic apparatus is dropped in the direction of an arrow 52 in FIG. 4C. In this case, as shown in FIG. 4C, a shock load F52 acts on the radiographic apparatus at the instant when the apparatus collides with the floor. If the number of convex portions of the support member 15 is N, the shock load acting on each convex portion is represented by F' (=F52/N). If the convex portion has a columnar shape as shown in FIG. 4A, the shock F' acting on the convex portion is directly transferred to the side surfaces of the convex portion. A large load acts on the convex portion and is directly transferred to an X-ray detection sensor 14 joined to the support member 15. If the shock F' is large, the convex portion may deform or the X-ray detection sensor 14 may be damaged. That is, such a shock may cause a failure.

In contrast to this, as shown in FIG. 4B, a side surface of the convex portion is provided with an inclination of an angle θ (rad) to form a conical shape, which disperses the shock load F' acting on the convex portion when the apparatus is dropped. The load component in the horizontal direction coinciding with the dropping direction is represented by F' cos θ, which is smaller than F'. That is, the shock on the X-ray detection sensor 14 also decreases. The load component of F' in the vertical direction is represented by F' sin θ, which coincides with the X-ray incident direction. A buffer material 13 can bear the force in this direction. Providing inclinations on the side surfaces of each convex portion in this manner will disperse the shock load F' into the components in the horizontal and vertical directions and allows the buffer material 13 to bear the load component in the vertical direction. In this case, the convex portions formed on the support member 15 do not easily deform, and the shock acting on the X-ray detection sensor 14 can be reduced. Using the structure of the support member 15 in the second embodiment makes it possible to provide a radiographic apparatus which achieves reductions in the thickness and weight of the apparatus and provides excellent convenience while securing strength necessary to protect the X-ray detection sensor placed inside the apparatus.

(Third Embodiment)

Figure 5A:
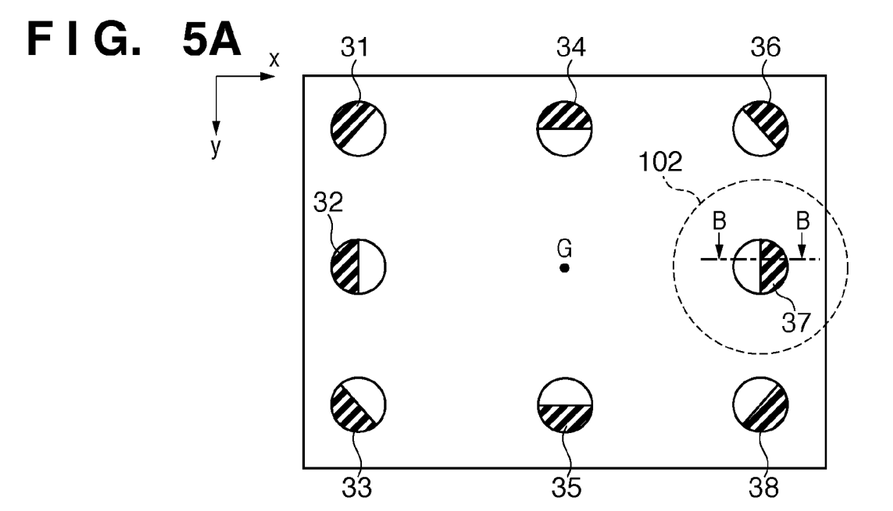
FIGS. 5A to 5D are views each showing an example of the shape of the concave portion of a support member used in a radiographic apparatus according to the third embodiment.

A support member used in a radiographic apparatus according to the third embodiment will be exemplarily described with reference to FIGS. 5A to 5D. Like FIG. 2A, FIG. 5A shows a support member 15 from the arrow Q direction in FIG. 1B. Although FIG. 5A shows a case in which the number of convex portions formed on the support member 15 is eight, the gist of the present invention is not limited to this number.

Figure 5B:
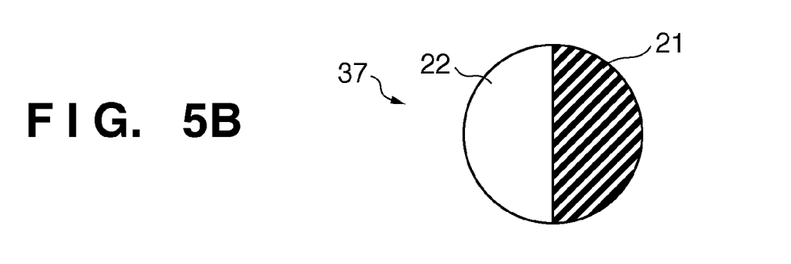
Figure 5C:
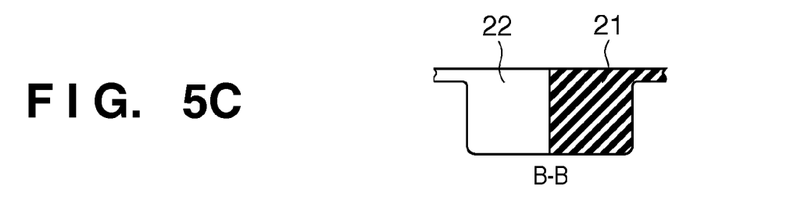

FIG. 5B is an enlarged view of a convex portion on a portion 102 in FIG. 5A. FIG. 5C is a sectional view taken along a line B-B in FIG. 5A. Each convex portion formed on the support member 15 includes the first member having the first longitudinal elastic modulus and the second member having the second longitudinal elastic modulus higher than the first longitudinal elastic modulus. An example of the first member is a portion 21 made of an elastic member such as a rubber member. An example of the second member is a portion 22 made of a rigid body. Overall, convex portions are arranged such that the portions made of the rigid bodies 22 face a central portion G (FIG. 5A) of the support member 15. The elastic portions 21 of the respective convex portions are arranged to face the circumferential direction of the support member 15 relative to the central portion G (FIG. 5A) of the support surface of the support member 15. The rigid bodies 22 of the respective convex portions are arranged to face the central portion G of the support surface of the support member 15.

Since the convex portions are constituted by the rigid bodies 22 and the elastic members 21 in this manner, when, for example, the apparatus is dropped in the direction of an arrow 51 in FIG. 4C and receives a shock load F51, the elastic members 21 of convex portions 33, 35, and 38 in FIG. 5A reduce the shock load. The rigid bodies 22 of convex portions 31, 34, and 36 can firmly bear the shock load. This makes it possible to protect an X-ray detection sensor 14 against a shock while reliably restricting the movement of the X-ray detection sensor 14 inside the radiographic apparatus.

When the apparatus is dropped in the direction of an arrow 62 in FIG. 4C and receives a shock load F62, the elastic members 21 of a convex portion 32 and the convex portions 33 and 35 in FIG. 5A reduce the shock load. The convex portions 34 and 36 and a convex portion 37 then firmly bear the shock load to protect the X-ray detection sensor against the shock while reliably restricting the movement of the X-ray detection sensor inside the apparatus.

As described above, each convex portion has the elastic member 21 to reduce a shock load acting thereon and the rigid body 22 to firmly bear the shock load and constrain deformation. Arranging such convex portions on a plurality of portions of the outer peripheral portion of the support member can suppress the force to bend the support member 15 due to a shock load. This makes it possible to also reduce the load acting on the X-ray detection sensor 14.

Figure 5D:
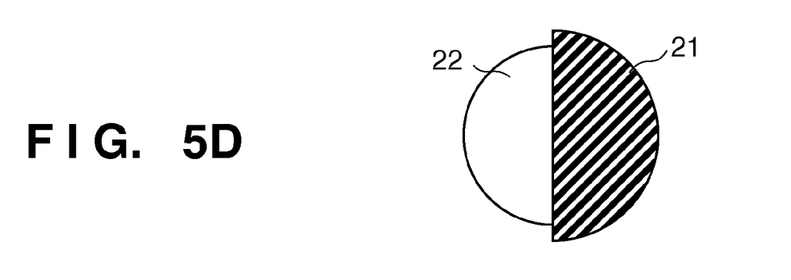

As shown in FIG. 5D, the convex portions of the support member 15 can engage with the concave portions of the second housing 16 in a pressurized state by making each elastic member 21 have a diameter (maximum outer diameter) larger than the diameter (maximum outer diameter) of the corresponding rigid body 22 having a size to engage with the corresponding concave portion of the second housing 16. Pressurizing them makes it possible to implement a tightly engaged state and hold the X-ray detection sensor 14 more reliably.

Using the structure of the support member described in the third embodiment makes it possible to provide a radiographic apparatus which achieves reductions in the thickness and weight of the apparatus and provides excellent convenience while securing the strength necessary to protect the X-ray detection sensor placed inside the apparatus.

(Fourth Embodiment)

The structure of a second housing 16 used in a radiographic apparatus according to the fourth embodiment will be exemplarily described with reference to FIGS. 7A to 7D and 8A to 8C. The second housing 16 has a structure that can bear the load received by the radiographic apparatus from the X-ray incident direction. The second housing 16 therefore needs to have strengths necessary to permit a load acting thereon and protect an X-ray detection sensor 14 inside the radiographic apparatus. If the second housing 16 is simply required to secure necessary rigidity, a material having a high longitudinal elastic modulus may be selected and the thickness of the second housing 16 may be increased. This however increases the weight of the second housing 16. That is, a reduction in weight cannot be expected. To secure necessary strength while reducing the weight, the second housing 16 is formed into a structure with a hollow structure (FIG. 7A).

Figure 7A:
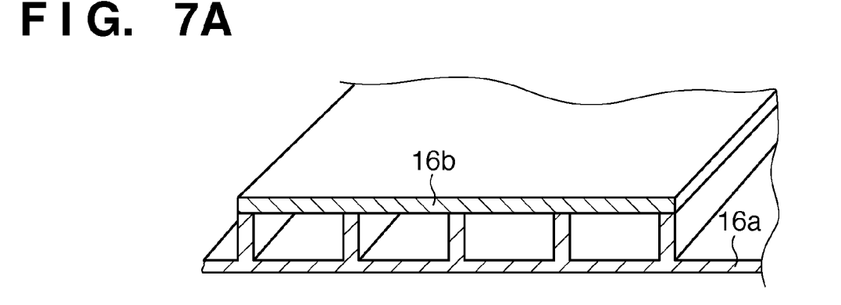
FIGS. 7A to 7D are views each showing an example of a hollow structure used in a radiographic apparatus according to the fourth embodiment.

As shown in FIG. 7A, the second housing 16 includes a housing 16a also serving as an exterior and a plate-like member 16b having a flat surface in contact with a support member 15. The housing 16a is joined to the plate-like member 16b with an adhesive or the like.

Figure 7B:
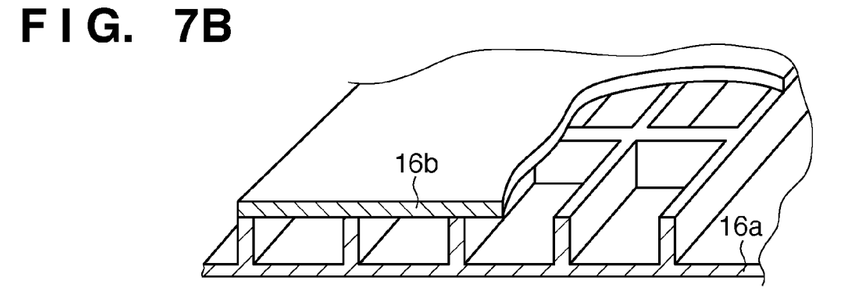
Figure 7C:
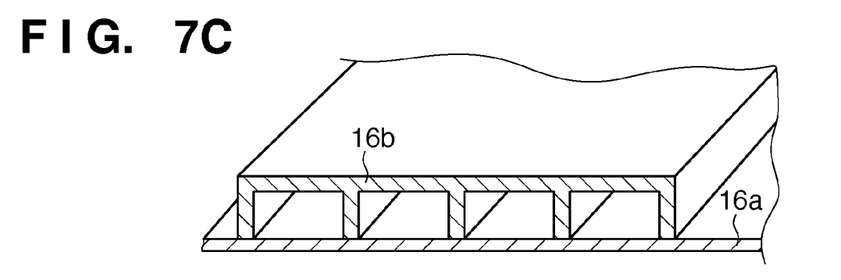

FIG. 7B is a partially cutaway view of the plate-like member 16b, exemplarily showing a rib structure integrally formed on the housing 16a. The plate-like member 16b is joined to the upper surfaces of the ribs to form a hollow structure. FIG. 7C exemplarily shows an arrangement in which a rib structure is integrally formed on the plate-like member 16b in contact with the support member 15 instead of the housing 16a. In this case, the lower surfaces of the rib structure are joined to the housing 16a to form the hollow structure.

Figure 7D:
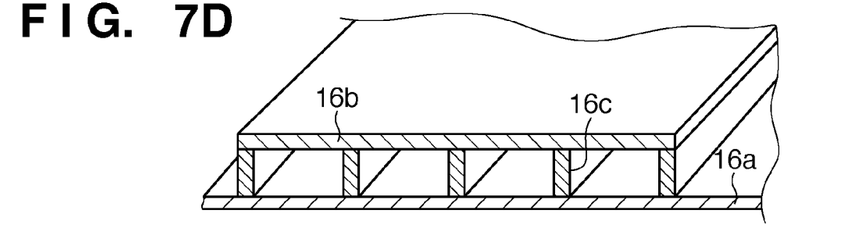

FIG. 7D exemplarily shows an arrangement in which a rib structure is formed by members 16c different from the housing 16a and the plate-like member 16b. The upper surfaces of the members 16c are joined to the plate-like member 16b, and the lower surfaces of the members 16c are joined to the housing 16a, thereby forming a hollow structure.

Figure 8A:
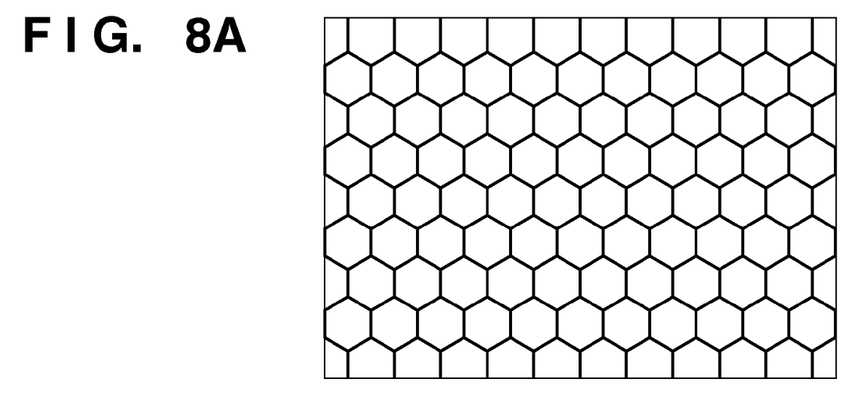
FIGS. 8A to 8C are views each showing an example of the rib shape of the hollow structure used in the radiographic apparatus according to the fourth embodiment.
Figure 8B:
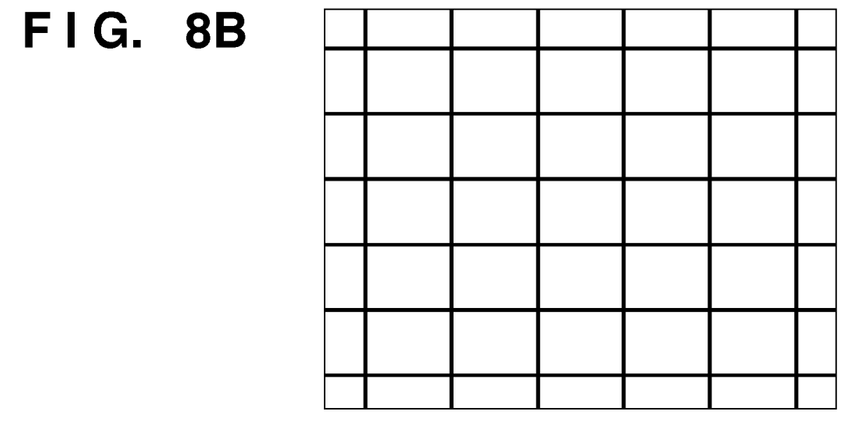
Figure 8C:
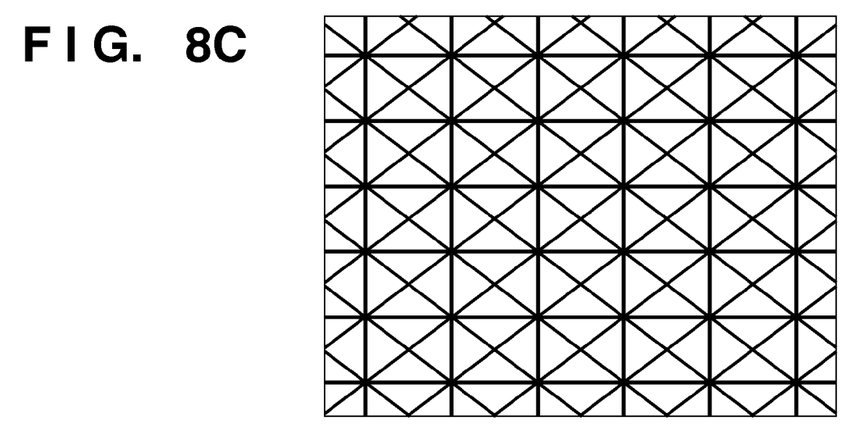

Various rib shapes are conceivable. For example, a hexagonal honeycomb shape is known well (FIG. 8A). Other rib shapes like those shown in FIGS. 8B and 8C are also conceivable. Forming the second housing 16 into a hollow structure makes it possible to provide a radiographic apparatus which achieves reductions in the thickness and weight of the apparatus and provides excellent convenience while securing the strength necessary to protect the X-ray detection sensor placed inside the apparatus.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g. computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-221441, filed Sep. 25, 2009, which is hereby incorporated by reference herein in its entirety.

The invention claimed is:

1. A radiographic apparatus comprising:
a first housing;
an X-ray detection sensor to detect an X-ray;
a buffer material which is placed between said first housing and said X-ray detection sensor;
a support member having a first surface to support said X-ray detection sensor, said support member being placed on an opposite side of said buffer material with respect to said X-ray detection sensor, wherein at least one convex portion is formed on a second surface on an opposite side to said first surface; and
a second housing which includes a concave portion engaging with said convex portion, wherein said concave portion has a depth that is greater than or equal to a height of said convex portion, and said second housing is configured to support a region other than said convex portion formed on said second surface of said support member, by a region of said second housing other than said concave portion.

2. The apparatus according to claim 1, wherein said buffer material is placed while receiving a first compression force from a contact surface in contact with said first housing and a second compression force from a contact surface in contact with said X-ray detection sensor in a direction opposite to that of the first compression force, and
wherein a height of said convex portion is larger than the amount of deformation caused in said buffer material by the first compression force and the second compression force.

3. The apparatus according to claim 1, wherein a tapered portion is formed on said convex portion such that a distal end portion of said convex portion has a smaller diameter than a proximal end portion of said convex portion, and
wherein a slope engaging with the tapered portion is formed on a side surface of said concave portion.

4. The apparatus according to claim 1, wherein said convex portion includes a first member having a first longitudinal elastic modulus and a second member having a second longitudinal elastic modulus higher than the first longitudinal elastic modulus.

5. The apparatus according to claim 4, wherein a maximum outer diameter of said first member is larger than a maximum outer diameter of said second member having a size to engage with said concave portion.

6. The apparatus according to claim 4, wherein said first member is placed to face a circumferential direction of said first member when viewed from a central portion of said first surface of said support member, and said second member is placed to face the central portion of said first surface of said support member.

7. The apparatus according to claim 1, wherein said second housing includes a hollow portion formed by a plurality of members.

8. The apparatus according to claim 1, further comprising a signal processing circuit board which is placed in said first housing and said second housing and is placed on a side surface of said X-ray detection sensor.

9. The apparatus according to claim 1, wherein a distal end portion of said convex portion is spaced from an internal end surface of said concave portion.

10. A radiographic apparatus comprising:
a first housing;
an X-ray detection sensor to detect an X-ray;
a buffer material located between said first housing and said X-ray detection sensor;
a support member having a first surface to support said X-ray detection sensor, with said X-ray detection sensor between said support member and said buffer material, wherein said support member has a second surface on an opposite side to said first surface, and has at least one convex portion provided on said second surface and extending away from said second surface by a height H; and
a second housing having a generally planar first surface facing said second surface of said support member, and having at least one concave portion formed in said first surface and extending from said first surface a depth D and engaging with said convex portion, wherein said depth D and said height H satisfy D>H.

11. A radiographic apparatus comprising:
a first housing;
an X-ray detection sensor to detect an X-ray;
a buffer material which is placed between said first housing and said X-ray detection sensor;
a support member having a first surface to support said X-ray detection sensor, and a second surface on an opposite side to said first surface, said support member being placed on an opposite side of said buffer material with respect to said X-ray detection sensor, wherein said second surface has at least one convex portion formed on said second surface and has at least one second portion that is not convex; and
a second housing which includes a first portion, which is a concave portion engaging with said convex portion, wherein said concave portion has a depth that is greater than or equal to a height of said convex portion, and said second housing has a second region that is not said first portion and that is configured to support said second portion of said second surface of said support member.

* * * * *